United States Patent [19]
Chambon et al.

[11] Patent Number: 5,817,503
[45] Date of Patent: Oct. 6, 1998

[54] METHOD FOR THE PREPARATION OF A PROTEIN BY YEASTS USING AN INDUCIBLE SYSTEM, VECTORS AND CORRESPONDING TRANSFORMED STRAINS

[75] Inventors: Pierre H. Chambon, Blaesheim; Daniel Metzger, Illkirch-Graffenstaden; John White, Strasbourg, all of France

[73] Assignee: Centre National de la Recherche Scientifique (C.N.R.S.), France

[21] Appl. No.: 453,888

[22] Filed: May 30, 1995

Related U.S. Application Data

[62] Division of Ser. No. 161,064, Dec. 3, 1993, abandoned, which is a continuation of Ser. No. 44,079, Apr. 6, 1993, abandoned, which is a continuation of Ser. No. 798,993, Dec. 2, 1991, abandoned, which is a continuation of Ser. No. 373,524, Jun. 30, 1989, abandoned.

[30] Foreign Application Priority Data

Jul. 1, 1988 [FR] France .................................. 88 08978

[51] Int. Cl.⁶ ............................. C12N 1/19; C12N 15/81; C12N 15/09
[52] U.S. Cl. ................. 435/254.2; 435/69.1; 435/172.3; 435/320.1
[58] Field of Search ............................. 435/320.1, 172.3, 435/254.2, 69.1

[56] References Cited

U.S. PATENT DOCUMENTS 5,071,773  12/1991  Evans et al. ............................. 436/501
5,175,105  12/1992  Meyhack et al. ........................ 435/215

FOREIGN PATENT DOCUMENTS 0258067  3/1988  European Pat. Off. .

OTHER PUBLICATIONS

Ma et al; Cell, vol. 51, Oct. 9, 1987; pp. 113–119.
T. Etcheverry et al; Biotechnology, vol. 4, No. 8; (Aug., 1986) pp. 726–730.
Metzger et al; Nature, vol. 334, Jul. 7, 1988, pp. 31–36.
Webster et al; Cell, vol. 52, Jan. 29, 1988, pp. 169–178.
Kakidani et al; Cell, vol. 52, Jan. 29, 1988, pp. 161–167.
Green et al; Nuc. Acid Res. 16, 369.
Krust et al; 1986 Embo J. 5, 891–897.
Feldman et al; 1982 Science 218, 297–299.
Cushing et al; 1986 Trans. Ill. Acad. Sci. 79, 111–116.
Burshell et al; 1984 J. Biol. Chem. 259 3450–3456.
Green et al; 1986 Nature 320, 134–139.
Strathern et al; 1981 "The Molecular of the Yeast Saccharomyces —Life Cycle and Inheritance" Cold Spring Harbor Laboratory, Cold Spring Harbor, N.Y., p. 99.
West et al; 1984 Molec. Cell. Biol. 4, 2467–2478.
Jost et al; 1984 Proc. Natl. Acad. Sci. USA 81, 429–433.
Feldman et al 1984 Proc. Natl. Acad. Sci USA 81, 4722–4726.
Feldman et al; Science 224, 1109–1111 (1984).
Martinez et al. 1987, Embo J. 6, 3719–3727.
Lech et al., "DNA–Bound Fos Proteins Activate Transcription in Yeast", Cell, vol. 52, Jan. 29, 1988, pp. 179–184.
Beato, "Gene Regulation by Steroid Hormones", Cell, Vo. 56, Feb. 10, 1989, pp. 335–344.
Pierrat, B, et al., Gene, 1992, 119, 237–245.
Heery, David et al., "Effcient transactivation by retinoic acid receptors in yeast requires retinoid X receptors," Proc. Natll. Acad. Sci. USA, vol. 90, pp. 4281–4285, May 1993.
Wright, Anthony P.H. et al., "Glucocorticoid–specific Gene Activation by the Intact Human Glucocortiod Receptor Expressed in Yeast," J.B.C., 1992, 11191–11195.
Schena et al. (1988) "Mammalian Glucocorticoid Receptor Derivatives Enhance Transcription in Yeast," Science 241:965–967.

*Primary Examiner*—Jasemine C. Chambers
*Assistant Examiner*—Scott D. Priebe
*Attorney, Agent, or Firm*—Cushman Darby & Cushman IP Group of Pillsbury Madison & Sutro LLP

[57] ABSTRACT

The present invention relates to a method for the preparation of a protein by yeasts, according to which:
  yeast cells which contain the following are cultured:
    a DNA sequence coding for the protein under the control of elements providing for its expression in yeasts, the elements comprising a transcription control sequence which is inducible by a complex formed by a receptor and a ligand,
    a DNA sequence which is functional in yeast, coding for the receptor, the receptor comprising two essential portions, one of which recognizes the ligand so as to form a complex with the ligand and the other binds to the said transcription control sequence; the portion of the receptor which recognizes the ligand is of higher eukaryotic origin, and the ligand is not necessary for the culturing of the cells but is capable of entering the cells when added to the culture medium,
  the ligand is added to the culture medium at an appropriate time point for induction,
  the synthesized protein is recovered.

6 Claims, 8 Drawing Sheets

METHOD FOR THE PREPARATION OF A PROTEIN BY YEASTS USING AN INDUCIBLE SYSTEM, VECTORS AND CORRESPONDING TRANSFORMED STRAINS

This is a division of application Ser. No. 08/161,064, filed Dec. 3, 1993 now abandoned which is a Rule 62 continuation of Ser. No. 08/044,079 filed Apr. 6, 1993 now abandoned, which is a continuation of Ser. No. 07/798,993 filed Dec. 2, 1991 now abandoned which is a continuation of Ser. No. 07/373,524 filed Jun. 30, 1989 (now abandoned).

BACKGROUND

The invention relates to inducible expression systems, to the corresponding transformed strains and to methods for obtaining them for producing proteins, in particular heterologous proteins, in yeasts.

The recombinant DNA technique enables genes for heterologous proteins to be expressed in yeasts. Thus, the construction of vectors containing yeast promoter sequences corresponding to the genes for glycolytic enzymes of *Saccharomyces cerevisiae*, such as 3-phosphoglycerate kinase (PGK), an alcohol dehydrogenase (ADH1) or glyceraldehyde-3-phosphate dehydrogenase (GPD), has enabled important proteins to be produced by fusion of their coding sequence to the yeast promoter, for example leukocyte interferon according to Hitzeman R. A. et al., Nature 293, 717–722 (1981) or hepatitis B surface antigen according to Bitter G. A. et al., Gene 263–274 (1984).

In many cases, it has been observed that the heterologous protein produced is toxic for the host cell, and leads to instability of the plasmids and the selection of cells which no longer express the protein in question. Methods enabling the expression of the gene for the protein to be repressed during the cellular growth phase, and then a high production of the protein to be induced during the final stage of culture, have been found using a promoter regulated by a change in carbon sources, for example the promoter of the galactokinase gene (GAL1) or the promoter of the uridinediphosphoglucose 4-epimerase gene (GAL10) which correspond to two of the four genes responsible for the utilization of galactose in yeast and whose expression is repressed by glucose and induced by galactose. Vectors comprising the GAL1 promoter linked to a heterologous gene have been described, enabling yeast to be grown in a medium containing glucose, and the protein then to be expressed when galactose is present in the medium. Yeast strains transformed with such vectors are described, for example, in British Patent Application 2,137,208, and these vectors, under the control of the GAL1 promoter, express in the presence of galactose proteins such as bovine growth hormone or prorenin. Most yeast promoters contain, upstream from TATA elements which mediate transcription initiation, elements which regulate transcription, "upstream activator sequences" (designated UAS), which represent the binding site of proteins which regulate transcription, such as GAL4 for the activation of the genes of galactose metabolism, these proteins themselves being under the control of their own promoters.

Different means have already been proposed for improving the efficiency of transcription of heterologous genes in yeasts. In particular, it has been proposed to use hybrid promoters which contain, upstream from the TATA element of a constitutive yeast promoter, an extrinsic UAS regulatory sequence, such as UASg which corresponds to the GAL1–GAL10 intergenic sequence and which is inserted, for example, upstream from the TATA element of a constitutive yeast promoter, such as GPD as described in Patent Application WO 86/00,680, or such as PGK as described in European Patent Application 258,067. The inserted UASg sequences enable the constitutive promoter to be successively repressed and then expressed by the carbon source used, such as glucose as a repressor and galactose as an inducer.

However, the use of promoters in general or of any hybrid promoter involves a control over totally repressed or induced levels, which is difficult to achieve because these levels involve a group of proteins which regulate transcription. Thus, the GAL4 gene activates transcription by the presence of galactose, which is directly or indirectly responsible for the dissociation of a complex between GAL4 and an antagonistic protein GAL80, while other proteins appear to be involved in the repression by glucose, such as GAL82 and GAL83 according to Yocum R. R. et al., MBC 4 1985–1998 (1984).

In addition to the drawbacks mentioned above, this type of system based on induction with galactose and/or repression with glucose is not very versatile; in effect, it cannot be used for yeasts which do not assimilate glucose and/or galactose and cannot be used in the case where one of these components constitute all or part of the carbon substrate of the culture medium.

It is hence advantageous to have available in yeasts inducing systems capable of being induced by products which are not in themselves necessary for the culturing of these cells, which is the case, for example, with hormones, in particular steroid hormones.

BRIEF DESCRIPTION OF THE FIGURES

In the attached figures,

FIG. 8 shows diagrammatically the construction of plasmid pTG3851, FIG. 9 demonstrates the effect on the activation of transcription in yeast cells of adding increasing quantities of estradiol with, as receptor, either the human estrogen receptor hERG (circles) or the human estrogen receptor hERG (triangles).

SUMMARY OF THE INVENTION

Thus, the present invention relates to a method for the preparation of a protein by yeasts, according to which:

yeast cells which contain the following are cultured:
- a DNA sequence coding for the said protein under the control of elements providing for its expression in yeasts, the said elements comprising a transcription control sequence which is inducible by a complex formed by a receptor and a ligand,
- a DNA sequence which is functional in yeast, coding for the said receptor, the receptor comprising two essential portions, one of which recognizes the ligand so as to form a complex with the said ligand and the other binds to the said transcription control sequence; the portion of the receptor which recognizes the ligand is preferably of higher eukaryotic origin, and the ligand is not necessary for the culturing of the cells but is capable of entering the said cells when added to the culture medium, the said ligand is added to the culture medium at an appropriate time point for induction, the synthesized protein is recovered.

DETAILED DESCRIPTION OF THE INVENTION

The expression of proteins by yeasts using recombinant DNA techniques is considered to be well known to those versed in the art. A considerable number of publications have already described the preparation of proteins, in particular heterologous proteins, by means of yeasts, using expression vectors. These expression vectors contain, more often than not, apart from the sequence coding for the said protein, the elements controlling its expression in yeasts, that is to say, in general, a promoter and a terminator.

In most cases, these vectors are nonintegrative vectors, that is to say plasmids; they then contain an origin of replication which is efficacious in yeasts, in particular the origin of the 2µ plasmid or an ars sequence peculiar to the said yeast.

These nonintegrative expression vectors contain, in addition, elements enabling provision to be made for their maintenance in the cells, either using as a selection marker a gene for resistance or alternatively an element complementing an auxotrophy of the host strain, URA3 or LEU2 for example.

In some cases, and in order to overcome the drawbacks linked to the use of self-replicating vectors, it has been possible to develop vectors providing for the integration of the sequences in question at chromosomal level. This type of vector enables a more stable strain to be obtained, but the amplification in respect of expression is sometimes smaller than with a nonintegrative plasmid.

Integration vectors contain, more often than not, at least one sequence homologous with a chromosomal sequence which will provide for exchange and integration.

It must be understood that, since the present invention relates essentially to the induction of transcription, the expression vectors which will be used can be of either the integrative or the nonintegrative type.

Although the method in question is more especially intended for the preparation of heterologous protein, it is possible to use it for expressing yeast proteins, in particular in the case of systems providing for the hyperexpression of a gene which can lead, in some cases to cell death before the optimum biomass is obtained.

"Heterologous protein" is understood to mean a protein foreign to the host cell which expresses it, that is to say different in origin from that of the host cell which, according to the invention, is a yeast. The protein can be of bacterial origin, for example Escherichia coli beta-galactosidase, or of higher éukaryotic origin, for example of human origin, such as, for example, lymphokines, blood coagulation factors, hormones, vaccinal antigens and, generally speaking, any protein of therapeutic or industrial interest.

As has been stated, the essential feature of the invention is the combination of a transcription control sequence and a receptor complexed to a ligand. The choice of the first is conditioned by the choice of the second.

Among usable transcription control sequences, there may be mentioned, in particular, the sequences which are usually functional in higher éukaryotic cells, that is to say natural sequences activating the transcription of higher éukaryotic cells, such as, for example, an HRE (for "hormone responsive element") or a variant or synthetic derivative of such a sequence, and which also fulfils in yeast this function of activation of transcription. These sequences are, in general, natural or synthetic, perfect or imperfect palindromic sequences.

Thus, for example, in the case where the transcription control sequence used is an HRE sequence, the receptor is the corresponding hormone.

As stated above, the transcription control sequence represents one of the elements providing for the expression of the desired protein in yeast. Provision for the expression in yeast may hence be made by hybrid sequences which comprise, apart from the transcription control sequence defined in the context of the invention, sequences corresponding to yeast promoter sequences. Among usable promoters, there may be mentioned the inducible promoter GAL1 referred to above, and also constitutive yeast promoters such as the PGK promoter.

In general, the TATA element of the promoter is retained and the transcription control sequence may be placed at variable distances upstream from the TATA element. It is especially advantageous to be able to have available a minimal structure for the hybrid promoter, that is to say a structure in which the distance between the TATA element and the transcription control sequence is small while remaining sufficient to provide for satisfactory inducibility.

"Receptor" in the sense of the invention is hence understood to mean a protein which is functional in higher éukaryotic cells, or variants or corresponding synthetic derivatives which display in yeast the functional properties of the native receptor.

The term "receptor" also comprises chimeric proteins, that is to say a structure in which the two essential portions are of different origins. For example, a preferred combination consists in preparing a hybrid receptor in which the portion which recognizes the ligand is of higher éukaryotic origin and the portion which binds to the transcription control sequence is of yeast origin, but it is possible to use sequences originating from any other microorganism, for example bacteria. The transcription control sequence then comprises a sequence which is functional in yeasts, that is to say a natural sequence activating transcription in yeasts. There may be mentioned, for example, the UAS of the GAL1 promoter, which is a yeast promoter.

The subject of the invention is hence the different functional combinations between a transcription control sequence, whether natural or derived, in particular, by chemical synthesis, and the receptor which can be a natural, derived or chimeric receptor. The nature of the ligand is, in turn, determined by the choice of receptor.

Among usable receptors, there should be mentioned nuclear receptors, in particular for a steroid, and other nuclear receptors, for example for retinoids or for thyroid hormones, as well as vitamin D3. The receptor for a steroid can be a natural receptor for steroid hormones, for example the estrogen receptor, the progesterone receptor or the testosterone receptor, or a variant receptor or chimeric derivative, which is functional with respect to the transcription control sequence. The steroid can be a natural steroid such as estradiol, progesterone or testosterone, or an analog or derivative, which is functional in the complex to which the transcription control sequence contained in the vector of the invention is sensitive.

The estrogen receptor can be the natural receptor (hereinafter designated hER) or a variant or chimeric derivative which is functional in the presence of estradiol with respect to the transcription control sequence contained in the vector of the invention.

More especially, the subject of the invention is the case where the essential portion of the receptor recognizing the ligand originates from the human estrogen receptor designated hERG which, compared with the receptor designated hER, has a glycine instead of a valine at position 400, the ligand then being estradiol. According to a feature of the invention, the whole of the hERG receptor may be used as the receptor.

Compared with the human estrogen receptor hER, the complementary DNA sequence of which had been published in Green S. et al. (1986) (Nature, 320, 134–139), the hERG receptor hence comprises a glycine in place of a valine at position 400.

It has been possible to observe that, by using this receptor instead of the hER receptor, a greater stability of the receptor was obtained, hence eliminating all risk of denaturation capable of leading to less binding of the specific ligand, in this instance estradiol. This phenomenon is expressly true in the region of 25° C., that is to say at the temperatures at which the method for the preparation of recombinant proteins comprising an induction stage according to the invention is carried out. It is hence preferable to use this receptor, which enables a smaller quantity of estradiol to be introduced into the culture medium in order to initiate the induction.

According to an additional feature of the invention, estradiol is added at a concentration of between 2 and 50 nM, and preferably of the order of 10 nM.

The invention relates especially to the case in which the control sequence is the sequence −605 to −634 of the chicken vitellogenin gene, which is the transcription control sequence of this gene, sensitive to estradiol (designated hereinafter ERE for "estrogen responsive element"). The synthesis of oligonucleotides containing this sequence or repetitions of the latter makes it possible to obtain, according to the invention, an expression vector comprising this sequence or repetitions of the latter (designated hereinafter ERE1 or ERE3).

One of the advantages of the invention is that the induction of the expression may be initiated very simply by adding to the culture medium a ligand matched to the receptor. The implementation of the induction hence becomes completely independent of the nature of the culture medium.

The appropriate time point for the introduction of the ligand can be determined easily; in practice, it will be the point at which a high level of biomass has been attained in the fermentation vat.

The invention relates most especially to the vectors, the structure and method for production of which will be given later by way of example in the experimental part.

It is appropriate to note that the elements for the expression of the protein and the elements providing for the expression of the receptor can occur on a single plasmid or on two different plasmids each containing an origin of replication which is functional in yeasts. However, it is also possible to arrange for the use of vectors providing for the integration of some of these elements, for example the production of the receptor can originate from sequences integrated on a chromosome of the cell.

Thus, the present invention also relates to the vectors carrying the sequences which are usable for the transformation of yeast cells.

The invention also encompasses the yeast strains which are usable in the method according to the invention.

As yeast strains, all strains customarily used for the production of recombinant proteins may be used. Saccharomyces strains such as *S. cerevisiae* may be mentioned, in particular. Special mention may be made of strains displaying one or more deficiencies in proteolytic activity, for example having the pep4 mutation. There may also be mentioned strains displaying a suppression of the proteolytic function encoded by the PRC1 gene. The use of these strains enables the quality of the proteins obtained to be improved.

The examples which follow illustrate the invention without, however, limiting the latter.

EXAMPLE 1

Construction of the pYERE/hER vectors Methods

The techniques of molecular biology used for the construction of the different plasmids are described in the manuals "Molecular cloning, a laboratory manual", T. Maniatis, E. F. Fritsch and J. Sambrook, Cold Spring Harbor, N.Y.: Cold Spring Harbor Laboratory (1982) and "Current Protocols in Molecular Biology", F. M. Ausubel, R. Brent, R. E. Kingston, D. D. Moore, J. A. Smith, J. G. Seidman and K. Sruhl, Greene Publishing Associates and Wiley Intersciences (1987). They comprise, in particular, digestion of the DNA with restriction enzymes, separation of the DNA fragments by agarose or polyacrylamide gel electrophoresis, ligation of DNA fragments with the enzyme T4 DNA ligase, transformation of *E. coli* with the recombinant plasmids and determination of the nucleotide sequence by Sanger's technique.

The plasmids used carry the gene for resistance to ampicillin, thereby permitting selection of the bacteria transformed by a plasmid on agar dishes containing ampicillin (50 $\mu$g/ml).

The *E. coli* strain used is strain DH5, genotype: F-, endA1, HsdR17(rk-md+), supE44, thi-1, lambda-, reca&, gyrA96, relAI (Hanahan: DNA cloning: a practical approach (Vol. 1=p. 109–135, ed. D. M. Glover, IRL Press, Oxford (1985)).

The techniques of transformation and growth of yeast strains are described in "Laboratory Course Manual for Methods in Yeast Genetics", F. Sherman, G. R. Find and J. B. Hicks, Cold Spring Harbor, N.Y.: Cold Spring Harbor Laboratory (1986).

The yeast strain used is TGY14-1a, pep4.3, genotype Mat a, ura3-251-373-328, leu2, pep4.3.

Figure 1:
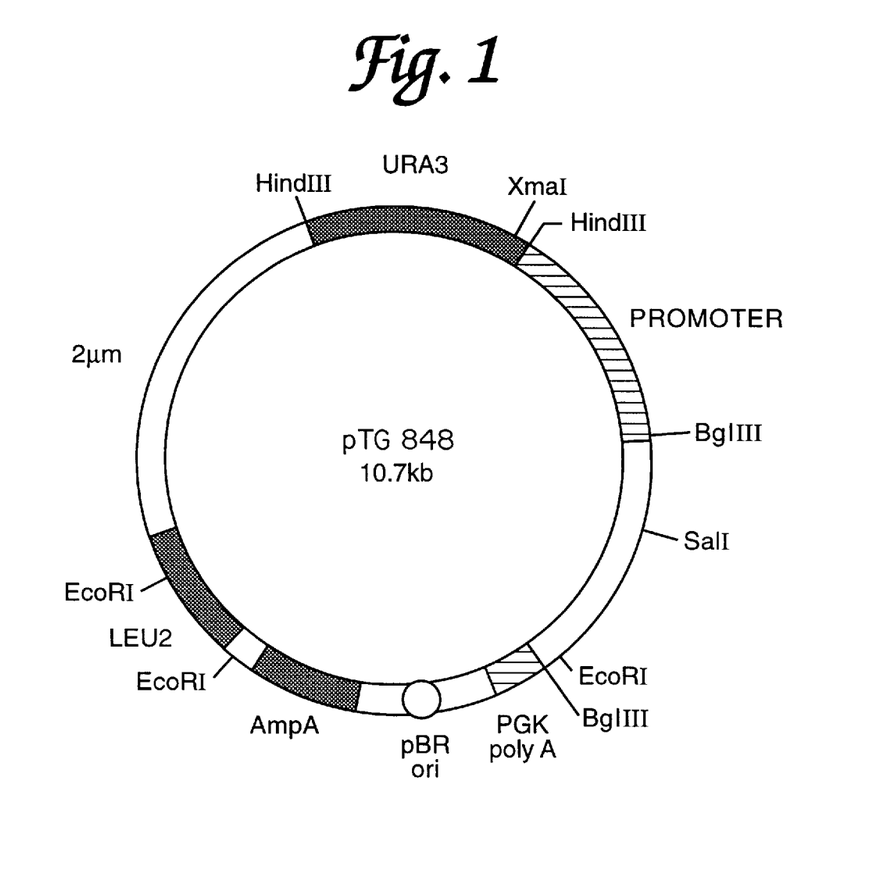
FIG. 1 shows the structure of pTG848.

The parent plasmid pTG848, described in European Patent No. 200,655, is an *E. coli*/yeast shuttle plasmid which permits the expression in yeast of an exogenous gene under the control of the phosphoglycerate kinase (PGK) gene promoter. This plasmid contains a pBR 322 origin of replication and the gene for resistance to ampicillin for selection in E. coli, and a 2 μm origin of replication and the ura3 and leu2 genes for selection in yeast, as well as the PGK gene promoter and its 3' end containing the polyadenylation signal. This gene was modified so as to introduce a BglII site at the initiation ATG, thereby enabling the coding region for another protein to be inserted between this site and the BglII site situated upstream from the polyadenylation signal (FIG. 1).

Construction of plasmids pUC18, ERE1, pUC18 EREm, pUC18 ERE3

Plasmid pUC18 (C. Yanisch-Perron, J. Vieira and J. Messing, Gene 33, 103–1190 (1986)) contains a pBR322 origin of replication, the gene for resistance to ampicillin and a polylinker comprising, in particular, XbaI and HindIII sites. This plasmid was digested with the restriction enzymes XmaI and HindIII; to the plasmid thus digested, the following are then added by complementary oligonucleotide techniques:

5'-CCGGGTCTAGAAGATCTA3'
3' CAGATCTTCTAGATTCGA5'

The derived plasmid pUC18 BglII then has a polylinker which contains, in order, XmaI, XbaI, BglII and HindIII sites.

Into this plasmid, digested with BglII, the fragments consisting of the following complementary oligonucleotides are introduced respectively:

ERE1: 5' GATCCAATATTCCTGGTCAGGCGTGACCGGAGCTGA3'
3' GTTATAAGGACCAGTCGCACTGGCCTCGACTCTAG5'
EREm: 5'GATCCAATATTCCCCGTCAGCGTGACCGGAGCTGA3'
3'GTTATAAGGGGCAGTCGCACTGGCCTCGACTCTAG5'

ERE3 which consists of a direct repetition of three ERE1 fragments.

ERE1 contains the ERE (for "estrogen responsive element") sequence −605 to −634 of the vitellogenin promoter.

EREm is a mutant in which a GC transversion in the ERE sequence considerably reduces its activity in MCF-7 cells.

Construction of plasmids pLRERE1, pLREREm, pLRERE3

Figure 2:
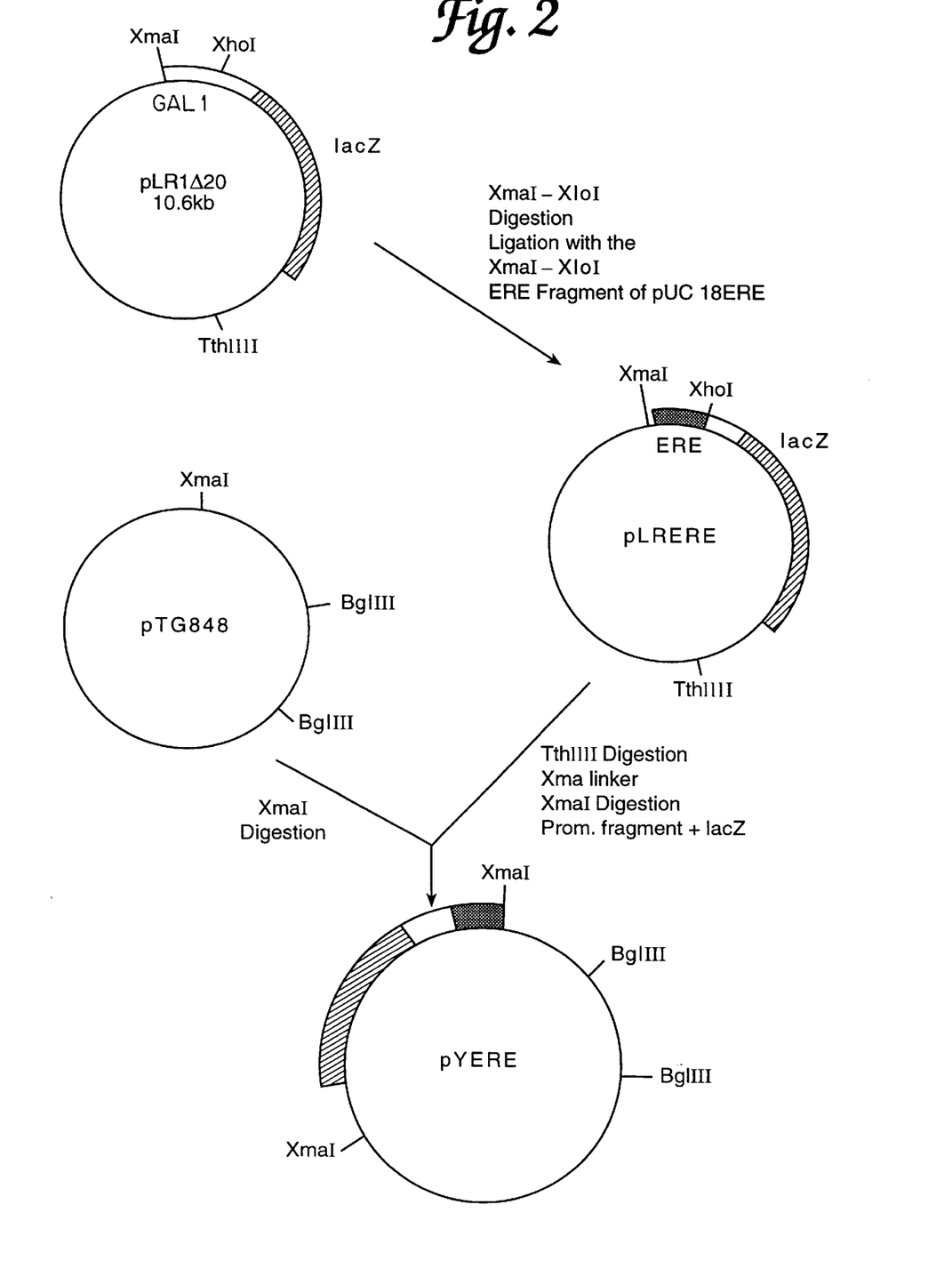
FIG. 2 shows schematically the strategy enabling pYERE to be prepared.

Plasmid pLR1Δ20 is described in the paper by R. W. West, R. R. Yocum and M. Ptashne, Molecular and Cellular Biology 4, 2467–2478 (1984). This plasmid contains an active and chimeric gene for beta-galactosidase under the control of the GAL1 promoter (FIG. 2).

The object of the construction is to replace the UASs (upstream activator sequences) of the Gal1 gene, situated between the XmaI and XhoI sites of the Gal1 promoter region, by the fragments ERE1, EREm and ERE3, respectively.

pLRERE1

Plasmid pUC18ERE1 is digested with the restriction enzyme BglII. The site is filled in with DNA polymerase I (Klenow fragment) in the presence of the 4 deoxynucleotide triphosphates. An XhoI linker (Biolabs ref. 1030) is then added to the ends: the plasmid is then digested with XmaI and XhoI and the XmaI-XhoI fragment containing the ERE1 sequence is isolated.

This fragment is then cloned into plasmid pLR1Δ20 between XmaI and XhoI sites to give plasmid pLRERE1.

pLREREm, pLRERE3

Plasmids pLREREm and pLRERE3 are constructed in the same manner by replacing pUC18ERE1 by pUC18EREm and pUC18ERE3, respectively, in the above protocol.

Construction of plasmids pYERE1, pYEREm, pYERE3

Plasmids pLRERE1, pLREREm and pLRERE3 possess a Tth111I site at the 3' end of the lacZ (beta-galactosidase) chimeric gene (FIG. 2). pYERE1:

Plasmid pLRERE1 is digested with the enzyme Tth111I; the site is then filled in with DNA polymerase I (Klenow fragment). An XmaI linker (Biolabs ref. 1048) is then added to the ends. The DNA is digested with XmaI, and the XmaI-XmaI fragment containing the lacZ chimeric gene under the control of the hybrid promoter (EREA-Gal1) is inserted at the single XmaI site of plasmid pTG848, to give plasmid pYERE1.

pYEREm, pYERE3

Plasmids pYEREm and pYERE3 are constructed in the same manner by replacing pLRERE1 by pLREREm and pLRERE3, respectively, in the above protocol.

Construction of plasmid pYGAL

Plasmid pLR1Δ20 is digested with the restriction enzyme Tth111I, and the site is then filled in with DNA polymerase I (Klenow fragment). An XmaI linker (Biolabs ref.1048) is added to the ends and the DNA is then digested with the enzyme XmaI. The XmaI fragment containing the lacZ chimeric gene under the control of the Gal1 promoter is inserted at the XmaI site of plasmid pTG848, giving plasmid pYGAL.

Construction of plasmids PYERE1/hER, pYERE1/hERR, pYEREm/hER, pYGAL/hER

Figure 3:
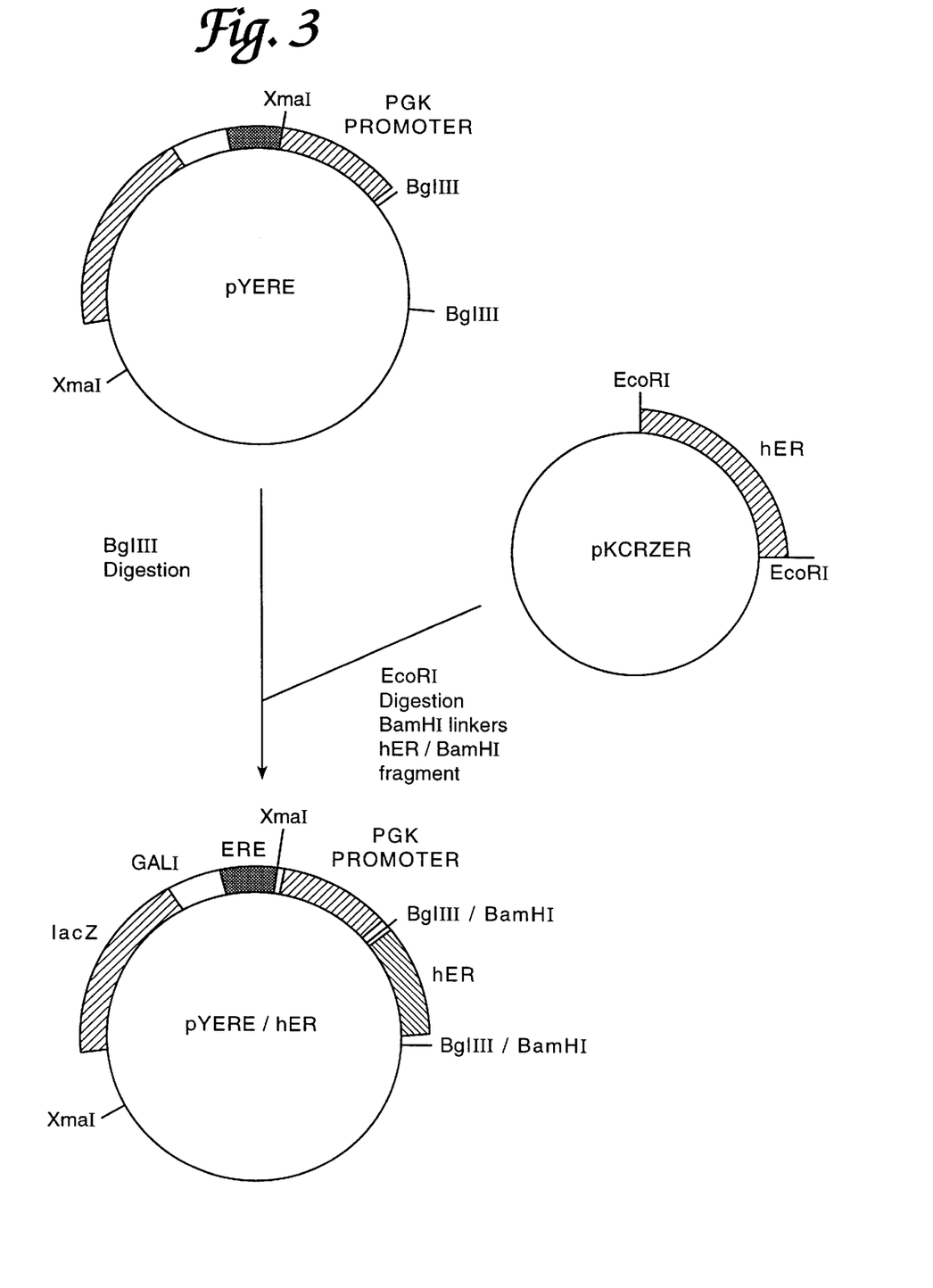
FIG. 3 shows schematically the strategy enabling pYERE/hER to be prepared.

The object of these constructions is to place the cDNA coding for the human estrogen receptor (hER) under the control of the PGK promoter, at the BglII site of plasmids pYERE1, pYEREm, pYERE3 and pYGAL (FIG. 3).

Plasmid pKCR2-ER containing the cDNA of the human estrogen receptor (S. Green et al., Nature 320, 134–139 (1986)) is digested with the restriction enzyme EcoRI and the site is then filled in with DNA polymerase I (Klenow fragment). A BamHI linker (Biolabs ref. 102) is then added to the ends. After digestion with BamHI, the fragment coding for the human estrogen receptor is isolated.

It is inserted into the vector pYERE1 digested with BglII to create plasmids pYERE1/hER and pYERE1/hERR, which differ by the orientation of the hER cDNA relative to the PGK promoter.

In pYERE1/hER, the PGK promoter is situated on the 5' side of the hER cDNA, and hence induces transcription of the mRNA coding for the hER protein.

In pYERE1/hERR, the orientation is reversed, and hence induces the transcription of an antisense RNA of the hER messenger RNA.

pYEREm/hER, pYERE3/hER and pYGAL/hER are constructed on the same model as pYERE1/hER, by replacing pYERE1 by pYEREm, pYERE3 and pYGAL, respectively, in the above construction.

Figure 4A:
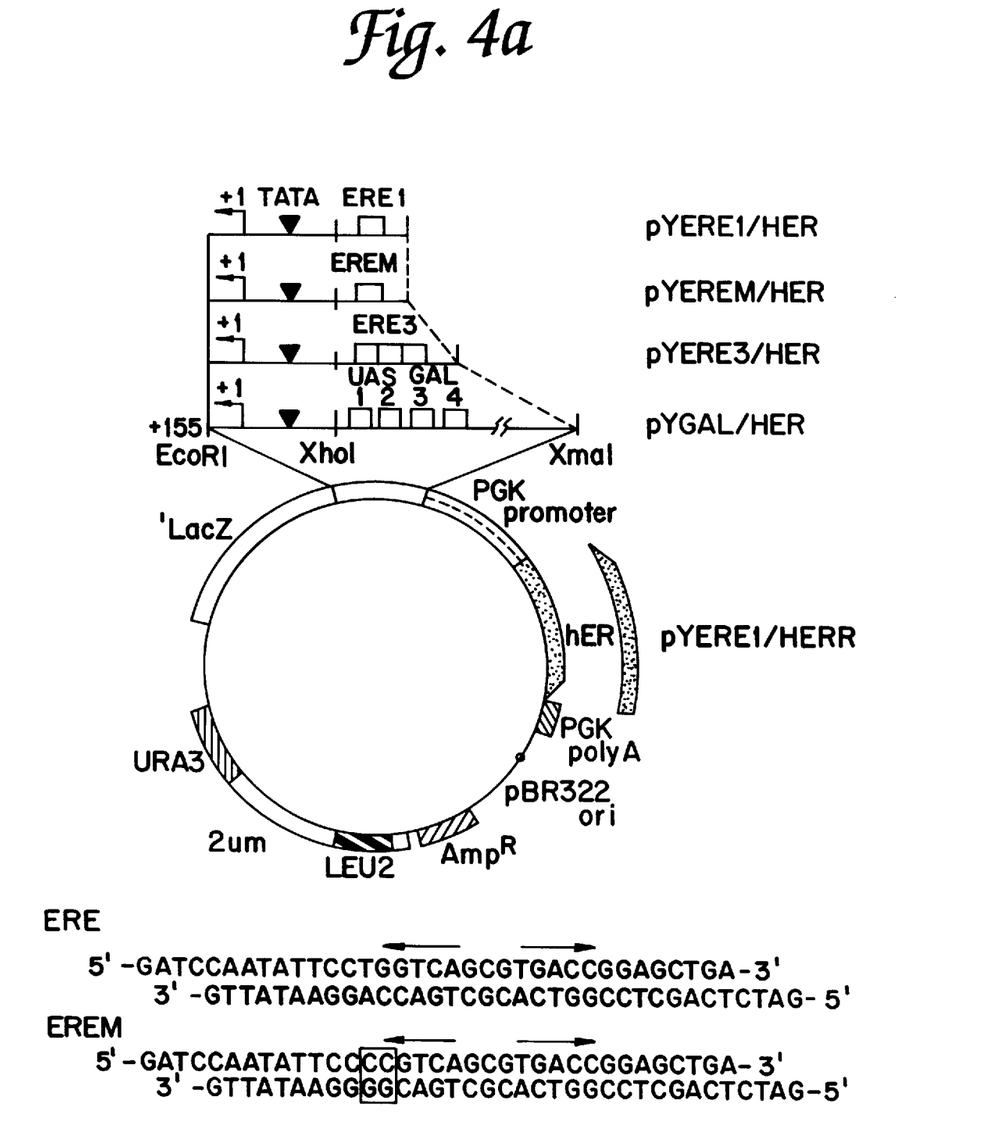
FIG. 4a shows schematically the structures of pYERE1/hER, pYEREm/hER, pYERE3/hER and pYGAL/hER and shows the sequences of the ERE and EREm elements.

These plasmids (FIG. 4a) constructed in E. coli DH5 are transferred into yeast strain TGY14.1a which carries the ura3 mutation. The presence of the ura3 gene on these plasmids permits complementation for the yeasts transformed by a plasmid, which are hence selected on agar dishes containing a medium without uracil (preparation: 0.67 g of Difco medium No. 0919–15, 0.5 g casamino acids, 1 g glucose, and 2 g agar per 100 ml).

EXAMPLE 2

Figure 4B:
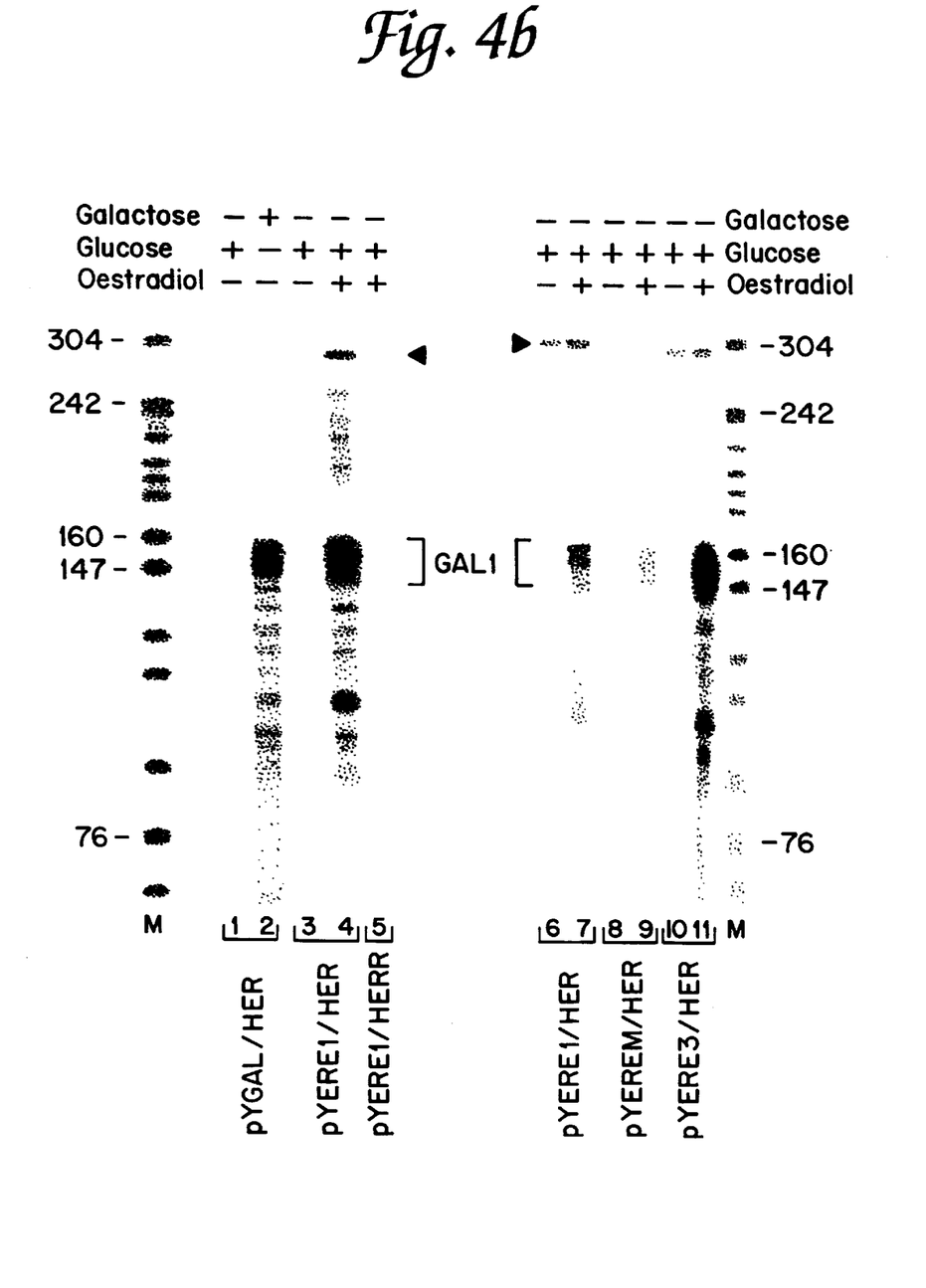
FIG. 4b shows, for the RNAs extracted from induced or noninduced cells containing the plasmids indicated, the RNA fragments protected from digestion by ribonucleases A and T1 after hybridization with an antisense Gall RNA probe.

Induction by estradiol of transcription for the ERE Gal1 hybrid promoters carried by the pYERE/hER vectors The different yeasts containing plasmids pYERE1/hER, pYEREm/hER, pYERE3/hER, pYERE1/hERR and pYGAL/hER, respectively, are cultured in base medium for yeast (Difco No. 0919–15) on the basis of 0.67 g/100 ml and 0.5% casamino acids containing 1% glucose or 2% galactose or 100 nM estradiol (added to the culture 2 hours before the cells are recovered) as shown in FIG. 4b.

The RNA is prepared from $10^9$ cells according to the protocol described in Methods in Yeast Genetics, p. 143–144.

To measure the transcriptional activity of the Gal1 or ERE-Gal1 promoters, these RNAs are hybridized with a radiolabeled RNA probe derived from the 5' end of the Gal1 gene (strand complementary to the messenger RNA). The hybridized fragments will be protected from digestion by RNases A and T1. The probe is prepared from the EcoRI fragment (containing the Gal1 promoter) of plasmid pLR1Δ20 (R. W. West, R. R. Yocum and M. Plashne, Molecular and Cellular Biology 4, 2467–2478 (1984)) cloned into plasmid Bluescribe M13+ (Stratagène ref. 211201). The resulting plasmid is then linearized with HindIII and the radiolabeled probe is then synthesized from the phage T7 promoter with Stratagène Kit No. 211604. The probe size is of the order of 1000 nucleotides.

There are several transcription initiation sites in the Gal1 promoter; the probe is complementary to the Gal1 RNA over a length of 154 to 165 nucleotides.

The probe is incubated with 20 µg of RNA, and the mixture containing possible hybrids is digested with ribonucleases A and T1 according to the protocol described in Current Protocols in Molecular Biology.

The undigested fragments are then identified by urea/polyacrylamide gel electrophoresis and autoradiography (FIG. 4b).

For the constructions expressing the hER receptor, the induction of a messenger RNA specific to the ERE-Gal1 hybrid promoter is observed in the presence of estradiol; the transcription initiation sites are identical to those of the Gal1 (pYGAL) promoter induced by galactose: protected fragments of the same size.

The induction of transcription using the ERE-Gal1 hybrid promoter is strictly dependent on the presence of estradiol. The induction by estradiol requires the presence of the hER receptor (the construction pYERE/hERR is inactive). It also requires the presence of an ERE element (for the construction pYGAL/hER, there is no induction by estradiol).

The quantity of Gal1 RNA detected for cells containing pYERE3/hER is approximately 10 times as high as for cells containing pYERE1/hER: the repetition in tandem of the ERE elements (pYERE3 contains an ERE trimer, pYERE1 a monomer) hence appears to have a synergistic effect on the activation of transcription.

EXAMPLE 3

Expression, inducible by estradiol, of beta-galactosidase in yeasts containing the pYERE/hER vectors Beta-galactosidase activity is measured according to the protocol of West et al. (1984). Table 1 below shows the beta-galactosidase activity of yeast strains carrying plasmids pYERE1/hER, pYERE3/hER, pYEREm/hER, pYERE1/hERR and pYGAL/hER, respectively, in the presence or absence of glucose, galactose or estradiol, as seen in the table.

The level of constitutive activity of the promoters is very low and is not affected by the presence of the hER protein (pYGAL and pYGAL/hER or pYERE1/hER and pYERE1/hERR give the same degree of activity). In contrast, the addition of estradiol leads to a strong induction of the hybrid promoters of pYERE1/hER and pYERE3/hER.

The fact that the promoters of pYEREm/hER and pYGAL/hER are not sensitive to induction by estradiol shows the necessity of a functional ERE element in the promoter controlling the expression of lacZ, while the absence of induction for pYERE1/hERR shows that the presence of the hER receptor is also necessary for observing induction by estradiol.

The level of expression attained in comparable to that obtained using the Gal1 promoter (the case of pYGAL/hER) in the presence of galactose.

The presence of three ERE elements in tandem (the case of pYERE3/hER) gives an activity twice as high as the case where the promoter contains a single ERE element (pYERE1/hER).

TABLE 1

Induction of beta-galactosidase activity by YhER in the presence of hormone

| PLASMID | MEDIUM | | | BETA-GALACTO-SIDASE ACTIVITY (units) |
|---|---|---|---|---|
| | Glucose | Galactose | Estradiol | |
| pYERE1/hER | + | − | − | 60 |
| pYERE1/hER | + | − | + | 1,060 |
| pYERE1/hERR | + | − | − | 60 |
| pYERE1/hERR | + | − | + | 60 |
| pYERE3/hER | + | − | − | 60 |
| pYERE3/hER | + | − | + | 2,060 |
| pYEREM/hER | + | − | − | 60 |
| pYEREM/hER | + | − | + | 260 |
| pYGAL/hER | + | − | − | 180 |
| pYGAL/hER | + | − | + | 180 |
| pYGAL | + | − | − | 180 |
| pYGAL | − | + | − | 2,300 |

The yeasts transformed by the plasmids indicated are cultured in the presence of 1% of glucose or 2% of galactose as stated in the table; for induction by estradiol, 100 nM hormone is added 2 hours before the cells are harvested.

The tests of beta-galactosidase activity are performed in a traditional manner (West R. W. Jr., Yocum R. R. and Ptashne M., Mol. Cell. Biol., 4, 2467–2478 (1984)).

EXAMPLE 4

Integration of a complementary DNA coding for hER in the genome of a yeast strain Preparation of the expression vector carrying a cassette for the expression of hER inserted into the PRC1 gene (pTG3809)

The cassette for the expression of hER is inserted into a fragment of the PRC1 gene in order to obtain, after transformation of a yeast strain with pTG3809, a yeast strain displaying elimination of the proteolytic function encoded by the PRC1 gene.

In the first place, a cassette for the expression of hER (M13TG2896) is prepared in the following manner:

the yeast PGK promoter (HindIII-BglII fragment) and its terminator (HindIII-BglII fragment) are introduced into phage M13TG130 (Kieny, M. P. et al. (1983), Gene 26, p. 91–99) linearized by HindIII digestion, to give phage M13 TG2890, the BamHI fragment derived from pKCR2-hER carrying the human estrogen receptor is introduced into M13TG2890 linearized by BglII digestion, to give a cassette for the expression of hER referred to as M13TG2896.

This cassette for the expression of hER is then inserted into the PRC1 gene to give plasmid pTG3809 permitting its integration in the yeast genome.

The sequence of the PRC1 gene has been published by Valls, L. A. et al. (1987) (Cell 48, p. 887–897). Two oligonucleotides are constructed from this sequence. The first is complementary to the 5' region of the gene, and its sequence is as follows:

5' AAG AAA GAC TGG GAC TTT GTG 3'

The second is complementary to the 3' region of the gene, and its sequence is as follows:

5' GAT TGG ATG AAG CCT TAC CAC 3'

From a yeast genomic library (chromosomal DNA fragments partially digested with Sau3A, inserted into the BamHI site of pFL1 (Parent, S. A. et al. (1985), Yeast 1, p. 83–138)), and by hybridization with these two oligonucleotides, an E. coli clone containing the PRC1 gene inserted into pFL1, and referred to as pTG2863, is selected.

Figure 5A:
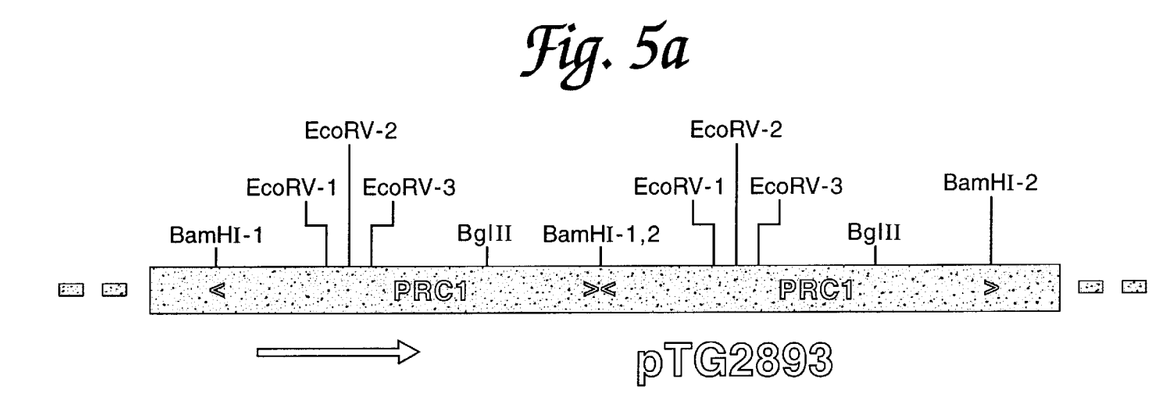
FIG. 5a shows diagrammatically the result of insertion in tandem of a portion of the coding sequence of PRC1 into pUC8 (BamHI site) to give pTG2893.

The 1.1-kb BamHI fragment of pTG2863 carrying a portion of the coding sequence of the PRC1 gene is introduced into the BamHI site of plasmid pUC8. This insertion takes place in tandem and plasmid pTG2893 (FIG. 5a) is obtained.

The coordinates of the first base of the restriction sites, relative to the adenine of the ATG of the PRC1 coding sequence, are as follows: BamHI-1: 482; EcoRV-1: 1102; EcoRV-2: 1153; EcoRV-3: 1234 and BamHI-2: 1574.

Figure 5B:
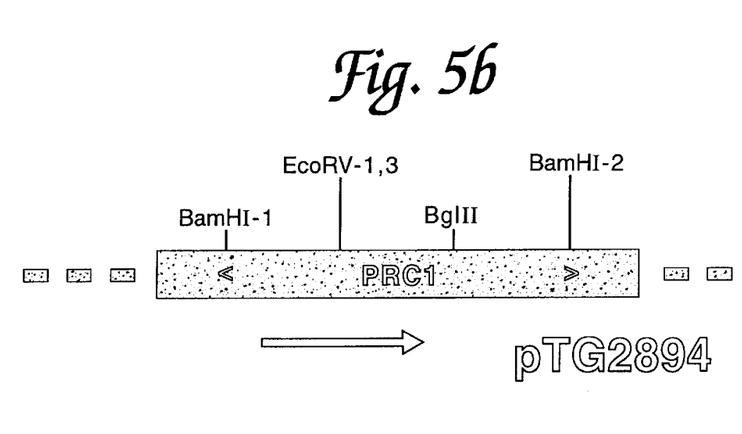
FIG. 5b shows schematically the deletion introduced into the fragment of PRC1 by excision of the EcoRV fragment of pTG2893 to give pTG2894, the arrows showing the direction of transcription.

A deletion in the PRC1 coding sequence is accomplished by EcoRV digestion of pTG2893 to give pTG2894 (FIG. 5b).

Figure 6:
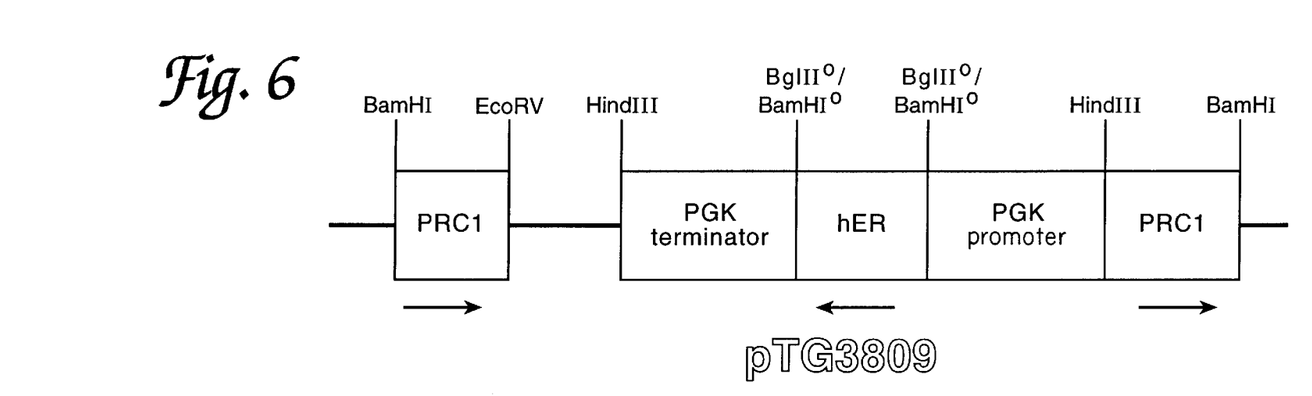
FIG. 6 shows the diagrammatic structure of plasmid pTG3809, the arrows showing the direction of transcription.

The cassette for the expression of hER is introduced into the deleted inner fragment of the PRC1 gene of pTG2894 in the following manner: the expression cassette (M13TG2896) is digested with BamHI, the ends are filled in with Klenow polymerase and, after cleavage with EcoRV, fragment is isolated. This fragment carries the complete cassette; it is introduced into the EcoRV site of pTG2894 to give plasmid pTG3809 (FIG. 6), which carries, between two fragments of PRC1:

several recognition sites for the restriction enzymes SphI, XbaI and KpnI originating from M13TG130, the PGK terminator yeast, the complementary DNA of hER, the PGK promoter of the yeast.

Transformation of the yeast strain with the plasmid carrying the hER expression cassette inserted into a fragment of the deleted PRC1 gene (pTG3809)

The yeast strain transformed is S. cerevisiae TGY2sp13b (MATa; ura3–251, –373, –328; leu2–3, –112).

Plasmid pTG3809 is cleaved with BamHI. The DNA sequences of the ends of the fragment thereby isolated are homologous with those of the PRC1 gene sequence. These sequences will enable the fragment to be integrated in the genomic portion of the PRC1 gene of the yeast strain. This insertion leads to destruction of the genomic PRC1 gene by deletion.

Since the fragment does not carry a selection marker, plasmid pLRERE3 is used as a cotransformation vector. It permits the selection of Ura⁺ prototrophs. Among Ura⁺ prototrophs, the clones which have integrated the hER expression cassette carry a mutation in the PRC1 gene which leads to a loss of activity of carboxypeptidase yscY. These mutants are detected by a colorimetric test (Jones, E. W. (1977), Genetics 85, p. 23–33). The structure of the modified PRC1 locus is verified by Southern's method.

This S. cerevisiae strain which has integrated the cassette for the expression of hER in the deleted PRC1 gene is referred to as TGY2sp13b prc1-d :: hER.

Construction of a plasmid carrying the ERE3 sequence and a fragment of the PGK gene promoter (pTG3851)

Figure 7:
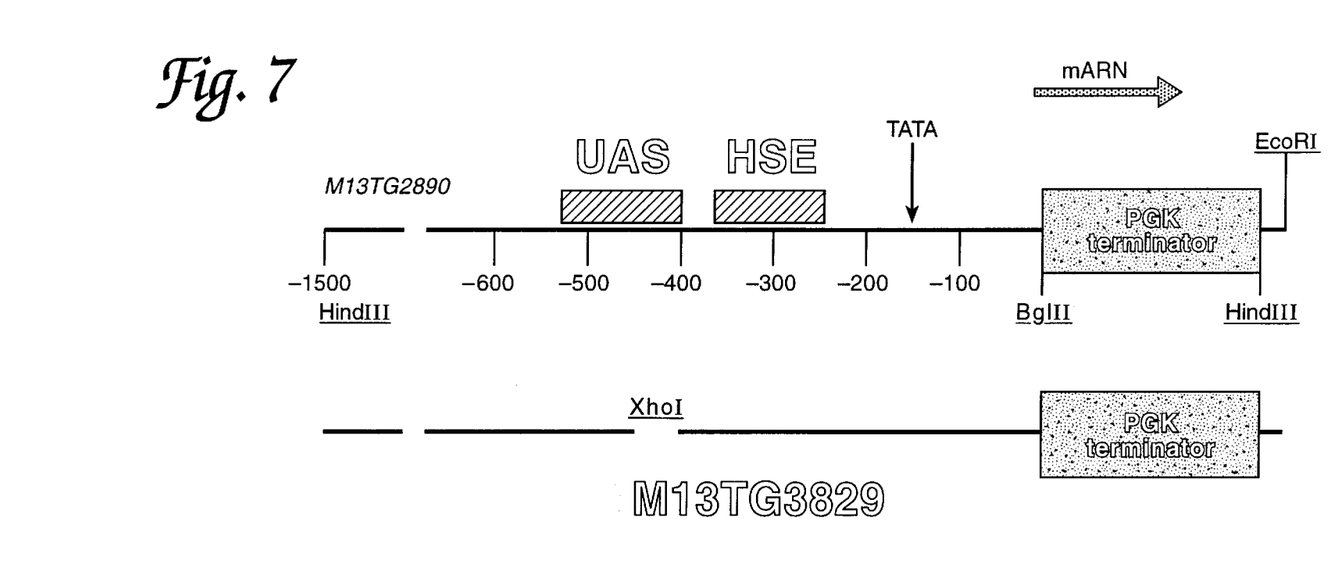
FIG. 7 shows the diagrammatic structure of phage M13TG2890.

An XhoI site is introduced into the vector M13TG2890 at the 5', 3' junction of the ends of the deletion accomplished by direct mutagenesis using the following oligonucleotide:

```
            —506  .    . —401
5' AATTACCGTCGCTCG AGCGACGGCTCACAG 3'
                 XhoI
``` to give the vector M13TG3829 (FIG. 7). The positions indicated are specified relative to the ATG of the PGK gene. The deleted form of the PGK promoter will be designed hereinafter PGK-dp401. The conformity of the sequence is then verified by sequencing.

This vector carries the TATA sequence and the transcription initiation site, the second activator sequence downstream designated HSE from –256 to –377 (Piper, P. W. et al. (1988), Nucleic Acids Res. 16, p. 1333), but no longer carries the UAS from –402 to –479. The XhoI site permits ligation with the ERE3 sequence, and the BglII site the introduction of a gene which enables an activity to be detected by an enzymatic test.

The host strain for the M13 phages is E. coli strain JM103 (delta(lac, pro), thi, strA, supE, endA, sbcB, hsdR, F'traD36, proAB, lacIQ, lacZdeltaM15).

Plasmid pLRERE3 is digested with XmaI and EcoRI. The DNA fragment containing the ERE3 sequences is purified on agarose gel and then inserted into the XmaI-EcoRI sites of plasmid pTZ18R (Pharmacia, LKB Biotechnology) to give plasmid pTG3833. The host strain for the plasmids is E. coli strain 1106 (supE, hsdR, hsdM, met, supF).

Phase M13TG3829 (FIG. 7) is treated with XhoI and EcoRI and is then inserted at the XhoI-EcoRI site of plasmid pTG3833 to give pTG3834.

The lacZ gene is excised from pCH110 (Hall, C. V. et al. (1983), J. Mol. Appl. Gen. 2, p. 101–109) by HindIII-BamHI digestion and cloned into pPolyII (Lathe, R. et al. (1987), Gene 57, p. 193–201) to give pTG1174. Plasmid pTG2145 corresponds to plasmid pTG1174 in which the HindIII, PstI and SalI sites have been eliminated. It contains, in a BglII-BamHI fragment, the following E. coli gene fusion: gpt :: trpS :: lacZ.

The sequences in the vicinity of the ATG are modified so as to permit the correct translation in yeast in the following manner:

pTG2145 is digested with BglII and KpnI and the 200-base pair fragment containing the ATG is purified on acrylamide gel;

this fragment is inserted at the BamHI-KpnI sites of phage M13TG131 (Kieny, M. P. et al. (1983), Gene 26, p. 91–99) to give M13TG3838;

the "AGC" sequence corresponding to the second codon for a serine of M13TG3838 is exchanged for the sequence "TCT", the cytosines at positions –3 and –1 relative to the ATG are replaced by adenines and a BglII site is generated on the 5' side of the ATG to permit a fusion with genes to be inserted downstream from the hybrid promoter, by performing a directed mutagenesis using the following oligonucleotide:

5' CGATGTATTTTTCAGACATTTTAA-GATCTCCAGCCTGTTT 3' to give phage M13TG3842. The bases modified during this mutagenesis are underlined below:

-GACACTTCACATGAGC- (M13TG3838)

-AGATCTTAAAATGTCT- (M13TG3842)

The 130-base pair BglII-KpnI fragment of M13TG3842 is introduced into pTG2145 to replace the 200-base pair BglII-KpnI fragment therein. Plasmid pTG3843 is thereby obtained.

Plasmid pTG848 (FIG. 1) is digested with BglII and then religated to give pTG2886. The large HindIII-EcoRI fragment of pTG2886 is ligated in the presence of T4 ligase BglII and the HindIII-EcoRI fragment of plasmid pFL1 (Parent S. A. et al. (1985), Yeast 1, p. 83–138) which carries a sequence of the *S. cerevisiae* plasmid, to give plasmid pTG2886 LEU2-d, URA3-d. The 0.9-kb HindIII fragment of plasmid pTG2800 described in the European publication of Patent EP-A-0,258,501 carrying the URA3-d gene is then inserted into the HindIII site of this plasmid to give pTG2886 URA3-d, delta LEU2-d. The SmaI-BglII fragment of M13TG131 (Kieny, M. P. et al. (1983), Gene 26, p. 91–99) which possesses several restriction sites is then introduced into this plasmid to give pTG3828.

Plasmid pTG3843 is digested with BglII and BamHI, and the fragment carrying the lacZ fusion gene is purified on agarose gel. This fragment is then inserted at the BglII site of pTG3846 (FIG. 8).

Figure 8:
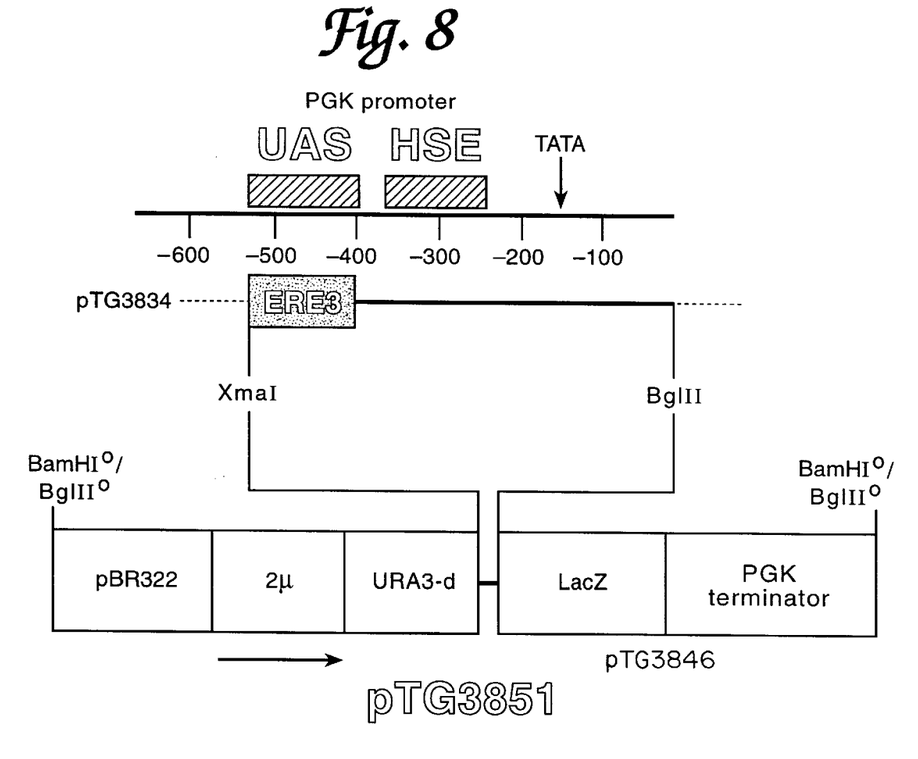

The plasmid pTG3834 is digested with XmaI and BglII, and the fragment is introduced into the XmaI and BglII site of pTG3846 to give plasmid pTG3851 (FIG. 8).

Inducible expression of lacZ

*S. cerevisiae* strain TGY2sp13b prc1-d :: hER is relieved of its cotransformation plasmid pLRERE3 and then transformed with plasmid pTG3851 by the lithium acetate method (Ito, H. et al. (1983), J. Bacteriol. 153, p. 163–168), and the Ura$^+$ prototrophs are selected. They are then cultured in an Erlenmeyer at 30° C. on a selective medium (0.7% of nitrogenous bases for yeasts without amino acids (Yeast Nitrogen Bases), 0.5% of casamino acids, 2% of glucose and, if necessary, 2% of agar). These cultures are set up with or without estradiol. For induction with estradiol, 100 nM hormone is added 2 hours before the cells are harvested. The cells are harvested, washed and ground in the presence of protease inhibitors, and the cell debris is then precipitated by centrifugation (10,000 rpm). The protein concentration is determined in the supernatant by the method described by Bradford (1976) (Anal. Biochem. 72, p. 248), and then the beta-galactosidase activity by the same assay method as that described in Example 3. The beta-galactosidase activity is also determined by the method used in Example 3; the assay is performed on permeabilized cells.

Table 2 shows the basal activity (in the absence of estradiol, [–(Est)]) and induced activity (in the presence of estradiol, [+(Est)]) of beta-galactosidase under the control of the ERE3 :: PGK-dp hybrid promoters. This activity is expressed as nmol of ONPG (O-nitrophenyl-beta-D-glucopyranoside) hydrolyzed per minute and per mg of protein at 30° C.; the values in brackets are directly comparable with those shown in Table 1, expressed in "units". The inducibility corresponds to the ratio specific activity without estradiol/specific activity with estradiol.

TABLE 2

| Vector: PGK promoter | Specific activity | | Inducibility |
|---|---|---|---|
| | – (Est) | + (Est) | |
| pTG3851:PGK-dp401 | 20 (30) | 460 (770) | 23 |

EXAMPLE 5

Preparation of a vector for the expression of beta-galactosidase in yeast which also carries a sequence coding for the hERG receptor (pYERE1/hERG)

The starting material is plasmid pYERE1/hER. Using the following oligonucleotide:

5'GGAGCACCCA<u>G</u>GGAAGCTACTGT-3'

A mutation in the GTG codon coding for valine in the complementary DNA coding for the human estrogen receptor (hER) is produced by localized mutagenesis in the following manner: the complementary DNA coding for the hER receptor described by Green et al. (1986) (Nature 320, p. 134–139) is subcloned into the EcoRI site of the eukaryotic expression vector pSG1 described by Green et al. (1988) (Nucl. Acids Res. 16, p. 369). The single-stranded DNA is then prepared and a point mutation is produced by localized mutagenesis in the GTG codon coding for valine at position 400 so as to obtain a GGG codon coding for glycine, using the oligonucleotide defined above (the change in nucleotide is underlined). The DNA sequences are verified. The vector pYERE1/hERG is then constructed by inserting the hERG complementary DNA into the vector pYERE1/hER.

EXAMPLE 6

Figure 9:
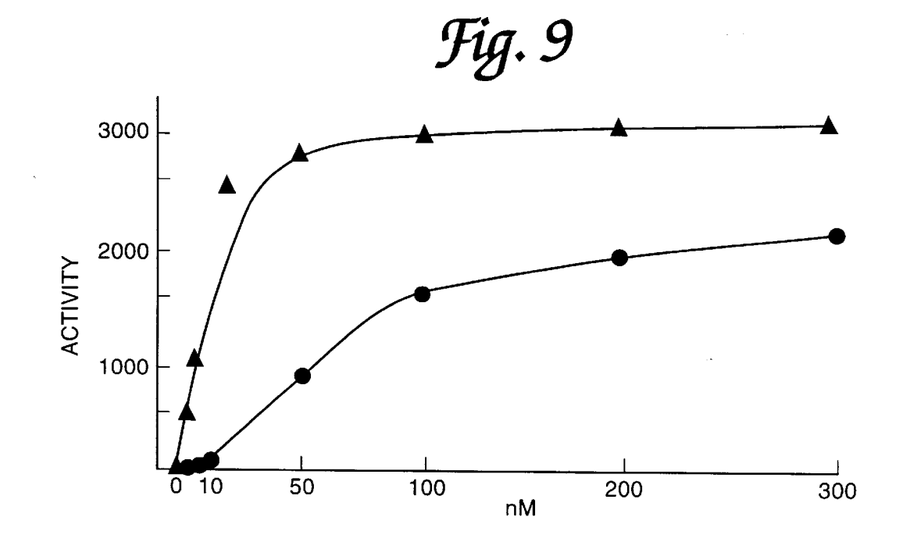

Expression, inducible by estradiol, of beta-galactosidase in yeasts containing the vector pYER1/hERG The conditions of transformation and culturing of the cells are identical to those described above. When the optical density reaches 600, 10 nM estradiol is added. FIG. 9 shows that 50% of the maximal beta-galactosidase activity is obtained for an estradiol concentration of 5 nM with pYERE1/hERG (triangles), whereas with pYERE1/hER (circles) a concentration of approximately 50 nM is required.

Moreover, it was possible to observe that the mutation which replaces val-400 by gly-400 in the estradiol-binding domain stabilizes the structure of the receptor and increases its affinity for estradiol to 25° C.

Saccharomyces strain TGY 14-1a pYERE3/hER was deposited with the Collection Nationale de Cultures de Microorganismes (CNCM) (National Collection of Microorganism Cultures) of the Institut Pasteur—25 rue du Docteur-Roux, 75724 Paris Cédex 15 (France) on 17 Jun. 1988 under No. I-770.

We claim:

1. An expression vector which is inducible to express a desired protein in yeast cells transformed by the vector, comprising:
   a DNA sequence coding for the protein, which sequence is under the control of an element providing for expression of the protein in yeasts, the element comprising
   a transcription control sequence of higher eukaryotic origin which controls transcription based on the presence of a complex formed by a receptor and its ligand, wherein the receptor is a natural nuclear receptor selected from the group consisting of a steroid receptor, a retinoid receptor, a thyroid hormone receptor, and a vitamin D3 receptor.

2. The expression vector of claim 1 further comprising a second DNA sequence encoding the receptor, said receptor being functional when the second DNA sequence is expressed in yeast cells.

3. The expression vector of claims 1 or 2, wherein the complex comprises a steroid receptor and its corresponding steroid.

4. The expression vector of claim 1, wherein the complex comprises an estradiol receptor and estradiol.

5. The expression vector of claim 1, wherein the transcription control sequence of higher eukaryotic origin comprises at least one copy of the sequence –605 to –634 of the chicken vitellogenin gene.

6. A yeast strain transformed by the expression vector of claim 1.

* * * * *